(12) United States Patent
Nguyen (10) Patent No.: US 7,604,588 B2
(45) Date of Patent: Oct. 20, 2009

(54) ERECTILE AIDE AND METHOD OF ATTACHING SAME

(76) Inventor: Bich Van Nguyen, 613 Pershing Dr., Silver Spring, MD (US) 20910-4341

( * ) Notice: Subject to any disclaimer, the term of this patent is extended or adjusted under 35 U.S.C. 154(b) by 219 days.

(21) Appl. No.: 10/445,011

(22) Filed: May 27, 2003

(65) Prior Publication Data
US 2004/0077925 A1    Apr. 22, 2004

Related U.S. Application Data

(63) Continuation-in-part of application No. 10/196,257, filed on Jul. 17, 2002, now abandoned.

(51) Int. Cl.
*A61F 5/00* (2006.01)
(52) U.S. Cl. ........................................ 600/38
(58) Field of Classification Search ............. 600/38–41; 128/842–844; 602/22, 30, 41–43, 52–54, 602/60, 61, 63, 75, 901
See application file for complete search history.

(56) References Cited

U.S. PATENT DOCUMENTS

| 4,424,808 A * | 1/1984 | Schafer et al. ................. 602/76 |
| 4,699,133 A * | 10/1987 | Schafer et al. ................. 602/77 |
| 4,785,802 A | 11/1988 | Blount |
| 5,221,251 A | 6/1993 | Edminster |
| 5,234,401 A | 8/1993 | Yamanaka |
| 5,360,390 A | 11/1994 | Maanum |
| 5,513,652 A | 5/1996 | Schwartz |
| 5,522,787 A | 6/1996 | Evans |
| 6,015,379 A | 1/2000 | Sachse |
| 6,024,761 A | 2/2000 | Barone et al. |
| D434,138 S | 11/2000 | DeVries |
| 6,193,753 B1 * | 2/2001 | Nordheim et al. ........ 623/11.11 |
| 6,251,067 B1 | 6/2001 | Strickholm |
| 6,308,709 B1 * | 10/2001 | Paul ........................... 128/844 |
| 6,309,344 B1 * | 10/2001 | Werner ........................ 600/41 |

FOREIGN PATENT DOCUMENTS

| DE | 134 368 | 1/1902 |
| DE | 875 853 | 5/1953 |
| DE | 724 3079 | 11/1972 |
| DE | 37 23 746 C2 | 5/1996 |
| DE | 296 03 248 U1 | 5/1996 |

* cited by examiner

*Primary Examiner*—Samuel G Gilbert

(57) ABSTRACT

An erectile aide includes a self-adhering elastic bandage which is coiled around the penis to prevent return of blood from the penis to the circulatory system. The self-adhering elastic bandage is then covered with a condom.

In accordance with another embodiment of the invention, the condom is placed over the penis first and then the self-adhering elastic bandage is coiled around the condom to prevent the return of blood from the penis. The tip of the condom is pulled down over the glans and shaft of the penis to overlie the self-adhering elastic bandage so as to expose the free end of the penis while protecting the bandage from moisture and mechanical stress.

14 Claims, 10 Drawing Sheets

Fig 9b: Top cut design

FIG. 10a

ERECTILE AIDE AND METHOD OF ATTACHING SAME

RELATED PATENT APPLICATION

This application is a continuation-in-part of U.S. patent application Ser. No. 10/196,275 filed Jul. 17, 2002, now abandoned.

FIELD OF THE INVENTION

The present invention is directed to erection aids. More particularly, the present invention is directed to mechanical erection aides.

BACKGROUND OF THE INVENTION

Some males lack the capability of achieving and maintaining an erection. Accordingly, there have been devices and methods employed to address this problem. Stiffening the penis surgically, for instance, by implanting a so-called penile prosthesis, is unacceptable to many men because of the constant problems this often entails. Moreover these expensive devices frequently fail to become properly implemented. Methods for erection improvement by means of injections of medications into the corpus cavernosum of the penis or by introducing medications into the urethra just before intercourse are also known. Methods and experiments are also known for constricting venous drainage from the corpora cavernosa, thus damming the flow, by placing a ring around the root of the penis in order to increase the turgor in the corpora cavernosa. The concern has also been addressed by using a tube placed in airtight fashion against the root of the penis to create a negative pressure in the tube that is intended to increase the volume of the penis. The air produced by creating the negative pressure is pumped into a ring that is seated at the root of the penis and when inflated is intended to reduce venous return.

Devices for stiffening the penis from outside are known. These devices are generally configured as tubular sheaths, liners and the like which act as braces for the body of the penis. These sheaths are largely rigid and if they are to be correctly applied must be individually selected from a great assortment of different sizes. Once applied, the inside diameter of these bracing devices cannot be changed again to adapt to the volume and turgor of the body of the penis. If the body of the penis is overly compressed when such a device is put in place, there is the risk of circulatory disturbances. The degree of repletion of the corpora cavernosa of the body of the penis and of the glans fluctuate very markedly, especially at the moment of sexual arousal, even in the man who has undergone surgery. If the degree of repletion, the turgor pressure, and thus the diameter of the glans decrease, then the glans can slip into the rigid tubular stiffening device during intercourse and thus prevent intercourse from continuing.

In German Patent DE-PS 134 368, the body of the penis is stiffened by wrapping a "bandage-like strip of fabric, covered on the inside by an adhesive composition" around the penis.

SUMMARY OF THE INVENTION

This invention is directed to an erection aid comprising a bandage and a condom, wherein the bandage is wrapped around the penis, and the penis with the bandage wrapped there around, is inserted into a condom.

In a further aspect of the invention, the bandage is a self-adhering elastic bandage with a pressure area.

In still a further aspect of the invention, the self-adhering elastic bandage has a selected length and a selected width with a portion of the width reduced by folding edges of the bandage over to provide a pressure area.

In still a further aspect of the invention, the bandage has length in the range of about 8 to about 10 inches; a width in the range of about 2 to about 3, inches and a thickness in the range of about 0.10 to about 0.15 inch.

In still a further aspect of the invention, a condom with a removable tip is slid over the penis at a location adjacent to the base of the shaft of the penis; an elastic, self-adhering bandage is wrapped around the penis over the condom. The top of the condom is then removed and the condom rolled back over the bandage, covering the bandage, covering the bandage while leaving the end portion of the penis shaft and glans uncovered.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

Figure 1:
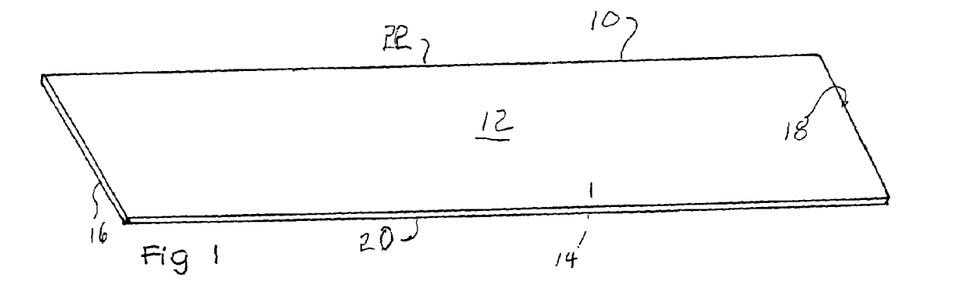
FIG. 1 is a top perspective view of a strip of elastic self-adhering bandage used to practice the principles of the present invention.

Referring now to FIG. 1 there is shown a strip of adhesive bandage 10 which is elastic. The strip of bandage 10 is in the range of about 8 to about 10 inches long, in the range of about 2 to about 3 inches wide, and in the range of about 0.1 to about 0.15 inches thick. The bandage 10 is a commercial product available at drug stores and preferably has a self-adhering adhesive incorporated into the fabric thereof. The bandages 10 has a first surface 12 which is an inner surface, a second surface 14 which is an outside surface, a first end 16, second end 18, and a first side 20 and second side 22.

Figure 1A:
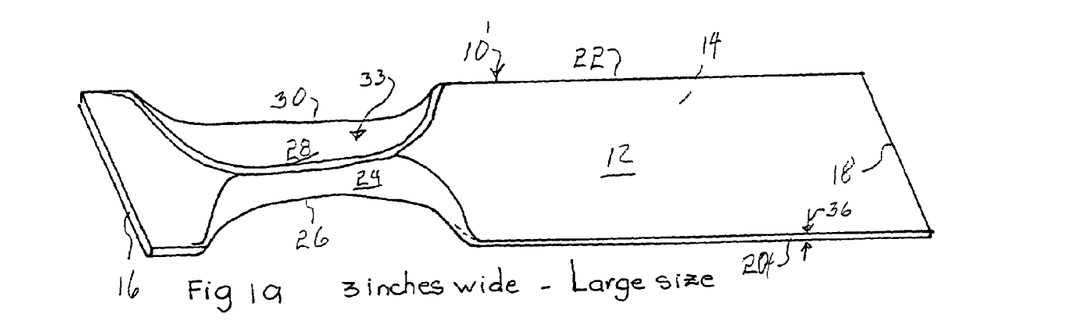
FIG. 1a is a perspective view of the bandage shown in FIG. 1 with portions of side edges thereof folded over a surface of the bandage.

Referring now to FIG. 1a, there is shown first embodiment 10' of the bandage which is relatively wide, i.e. about 3 inches and relatively long, i.e. about 10 inches. The first edge 20 has a portion 24 which is folded over the inside surface 12 and adheres thereto because the bandage 10 is self-adhering. The fold forms a crescent shaped crease 26 in the side 20 of the bandage 10. The second side 22 of the bandage 10 has a second portion 28 which is folded along a crease 30 and overlies the first side 12 of the bandage and portion 24 to form pressure portion 33 having a thickness which is increased with respect to the thickness 36 of the remainder of the bandage 10.

Figure 1B:
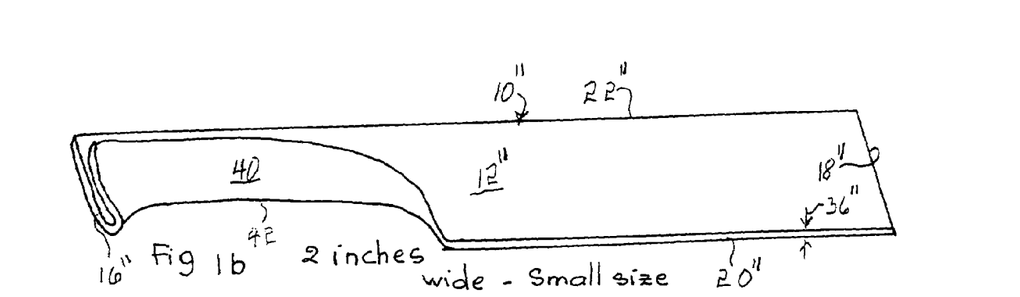
FIG. 1b is a perspective view of an adhesive bandage shown in FIG. 1 with one side edge folded over a surface of the bandage.

FIG. 1b illustrates a second embodiment of the invention wherein the bandage 10" is about 2 inches wide as opposed to 3 inches for the bandage 10 of FIG. 1. In that this embodiment is of a smaller size adhesive bandage 10", only one edge, side edge 20' has a portion 40 folded over onto the surface 12" at a crease 42. The edge portion 40, like the edge portions 24 and 28 form a pressure portion 44 on the elastic bandage 10".

Figure 2:
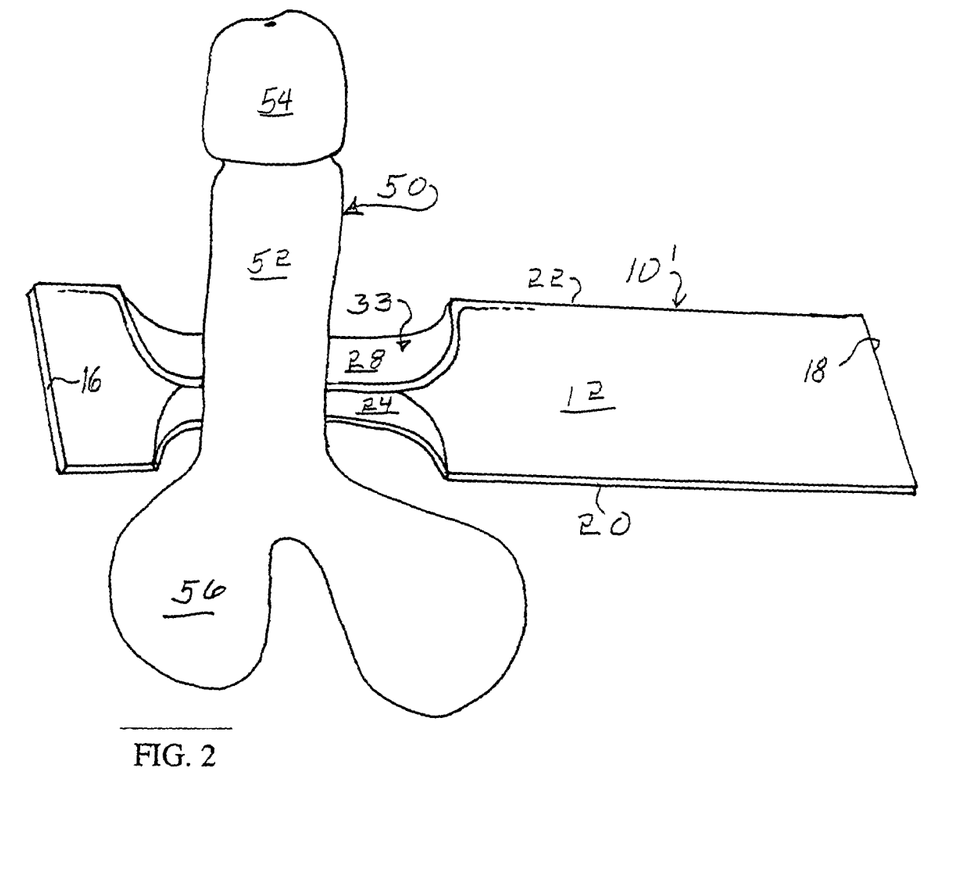
FIG. 2 is a perspective view of the bandage of FIG. 1a disposed adjacent to a penis.

Referring now to FIG. 2 which shows a top view of a penis 50 having a glans 52 and a head portion 54, the elastic bandage 10' of FIG. 1A positioned beneath the bottom of the penis shaft with the pressure portion 33 (or 44) engaging the underside of the penis shaft at a location between the testicles 56 and glans 54.

Figure 3A:
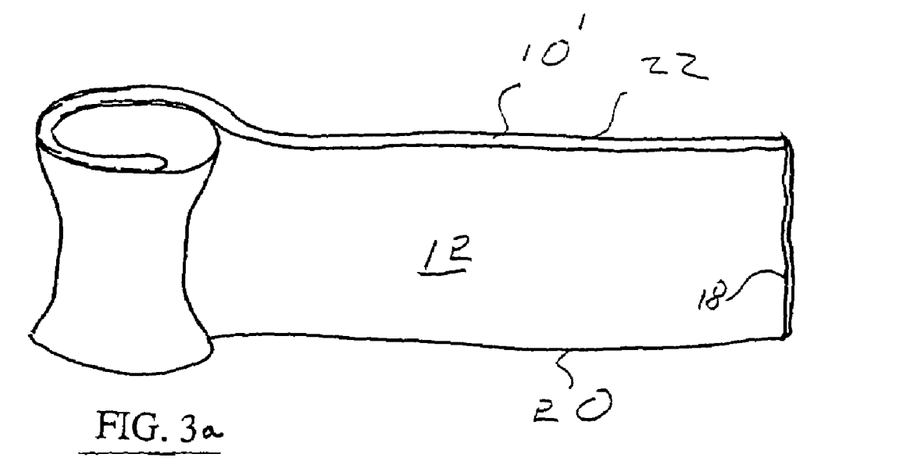
FIG. 3a is a perspective view of the elastic bandage being uncoiled.
Figure 3B:
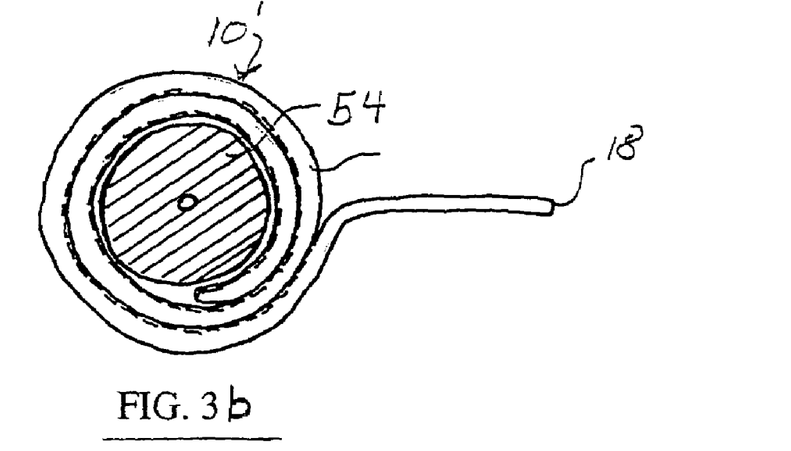
FIG. 3b is an elevation showing a section of a penis with a bandage according to FIGS. 1-3 being coiled about the penis of FIG. 2.

As is seen in FIGS. 3 and 3a, the elastic bandage 10, 10' or 10" is coiled about the penis shaft 54 in order to constrict the penis shaft.

Figure 4:
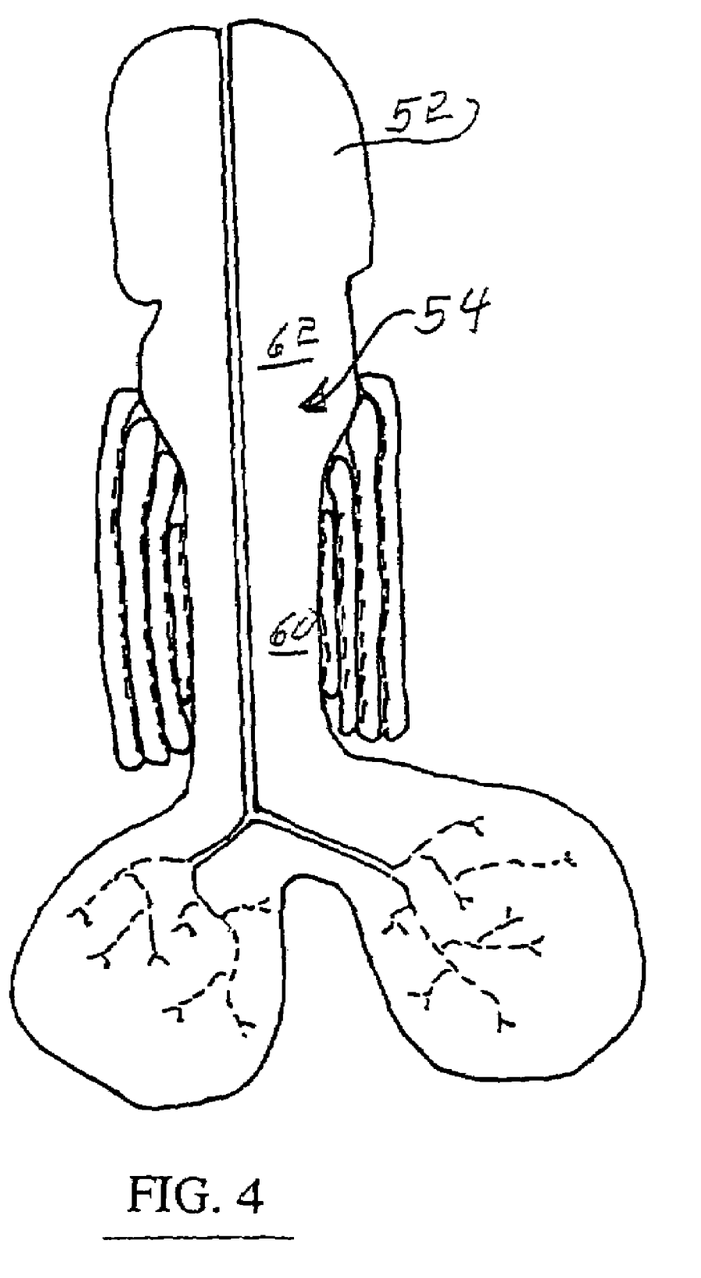
FIG. 4 is an elevational view showing a section of the bandage of FIGS. 1-3 coiled about a penis.
Figure 5:
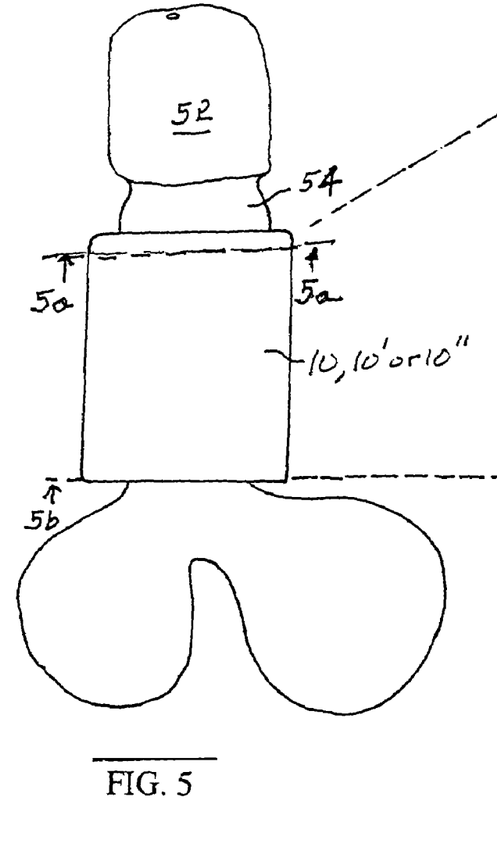
FIG. 5 is a bottom view of a penis with a length of bandage coiled there around.
Figure 5A:
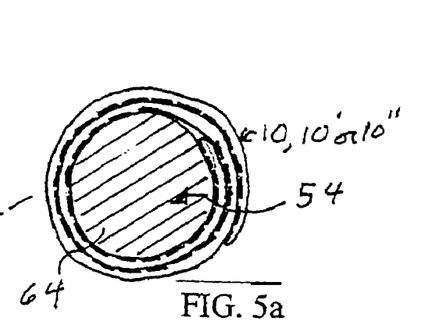
FIG. 5a is an elevation taken at line 5a-5a of FIG. 5.
Figure 5B:
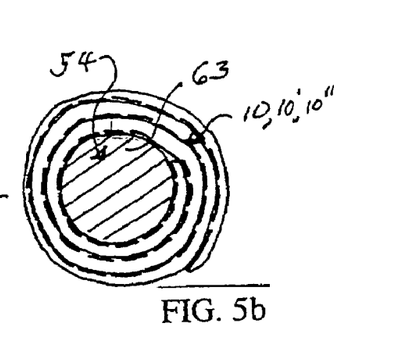
FIG. 5b is an elevation taken at line 5b-5b of FIG. 5.

As is seen in FIG. 4, the penis shaft 54 has a constricted area 60 and unconstricted area 62 upon coiling the bandage 10, 10' or 10" around the penis shaft 54. It is further evident from FIGS. 5 5a and 5b that under increased the base 63f the shaft of the penis is more constricted than the area 64 adjacent the head 52 of the penis. Note that in FIG. 5b the diameter of the penis shaft 54 is less than the diameter of the penis shaft adjacent the head 52.

Figure 6:
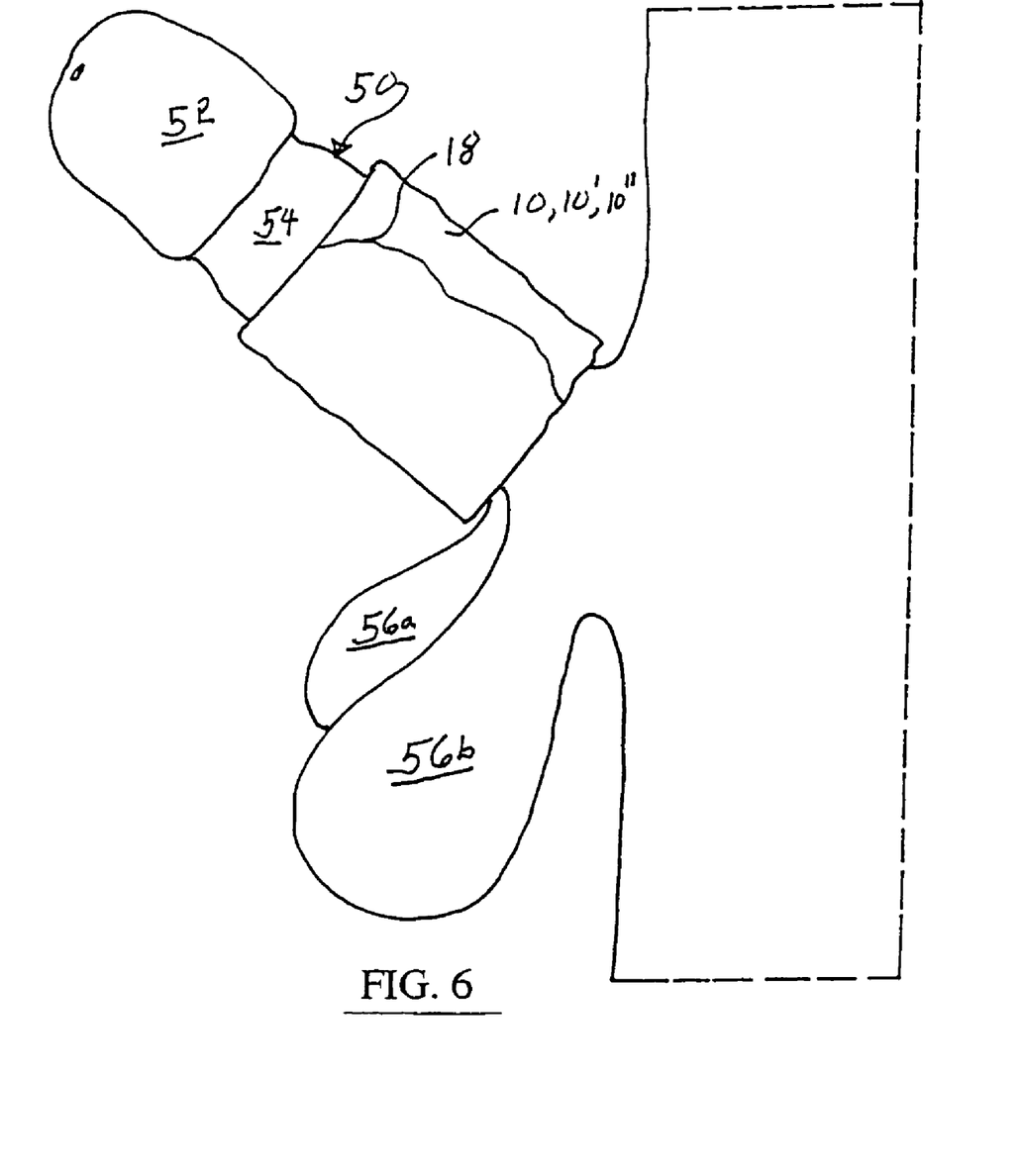
FIG. 6 is a side view showing an erect penis with the erection aid of the present invention holding the penis at attention.
Figure 7:
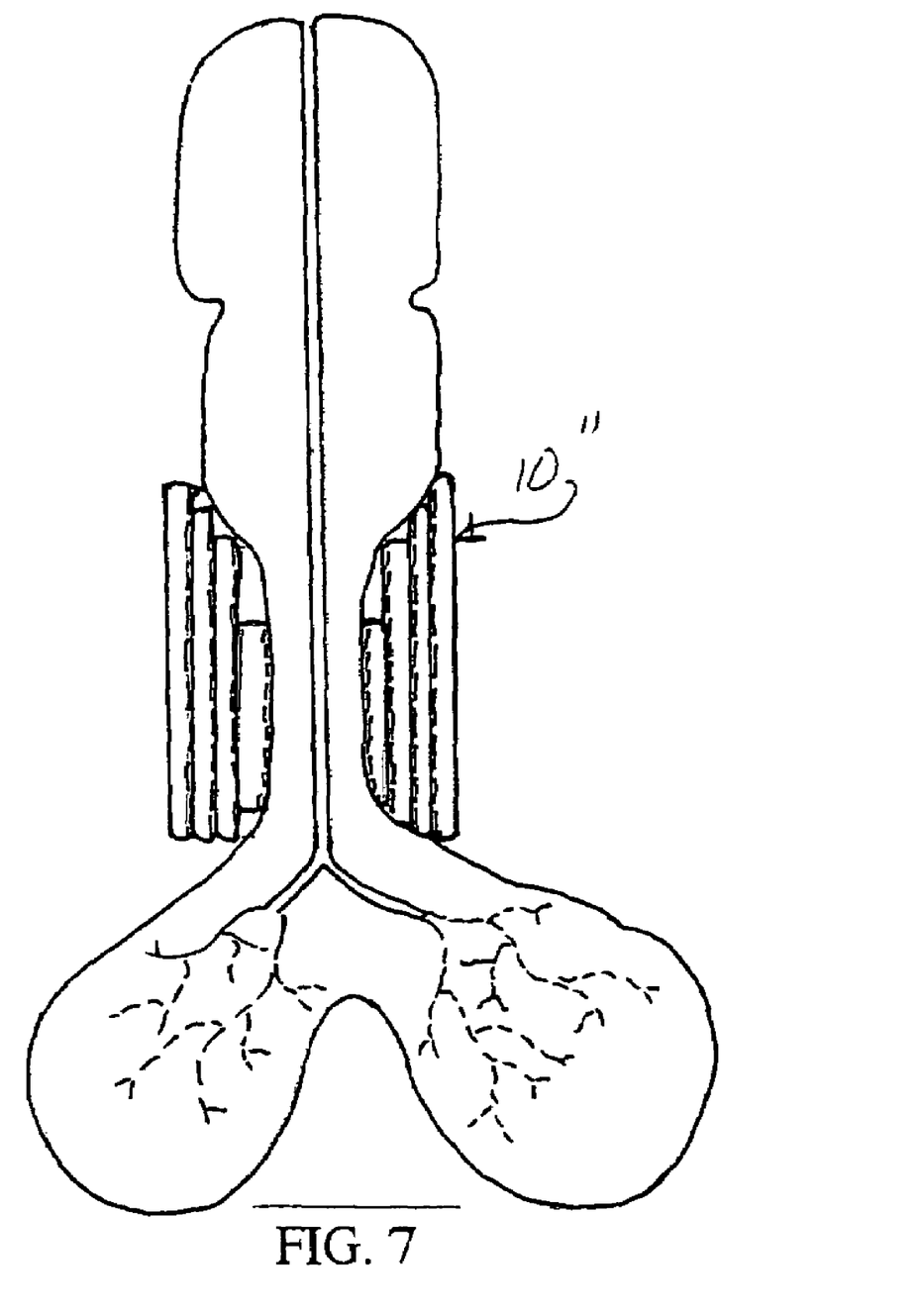
FIG. 7 is an elevation taken along lines 7-7 of FIG. 6.
Figure 8:
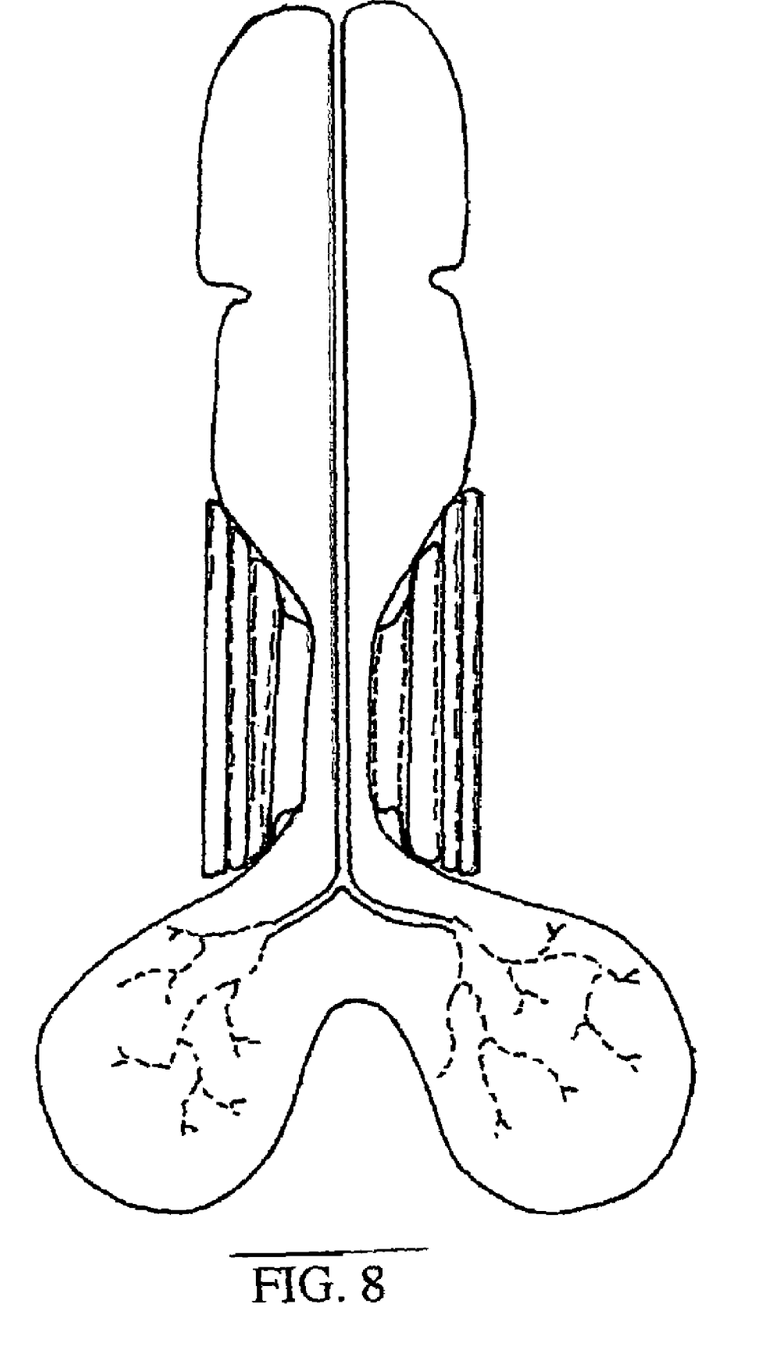
FIG. 8 is an elevation similar to FIG. 7 showing the erectal aid tightly constricted about the penis.

Referring now to FIGS. 6-8, it is seen that the high pressure portion 33 and 40 are closer to the base of the penis shaft 54 than the rest of the bandage 10', or 10" allowing the portion 63 of the penis shaft 54 to remain at a larger diameter for satisfactory sexual intercourse. As is evident from FIGS. 6 and 8, the diameter of the coil formed by the adhesive, elastic bandage 10 can be substantially the same as the diameter of the penis shaft 54 and perhaps only a little greater.

By not allowing blood in the penis to return from the penis back to the heart, the bandage 10, 10' or 10" traps blood in the penis. Upon comparing FIGS. 7 and 8 it is seen that by constricting the penis tighter with the bandages 10' and 10", blood is urged from the back of the shaft 54 toward front of the shaft. This both elongates and laterally enlarges the penis to the delight of some people.

Figure 9A:
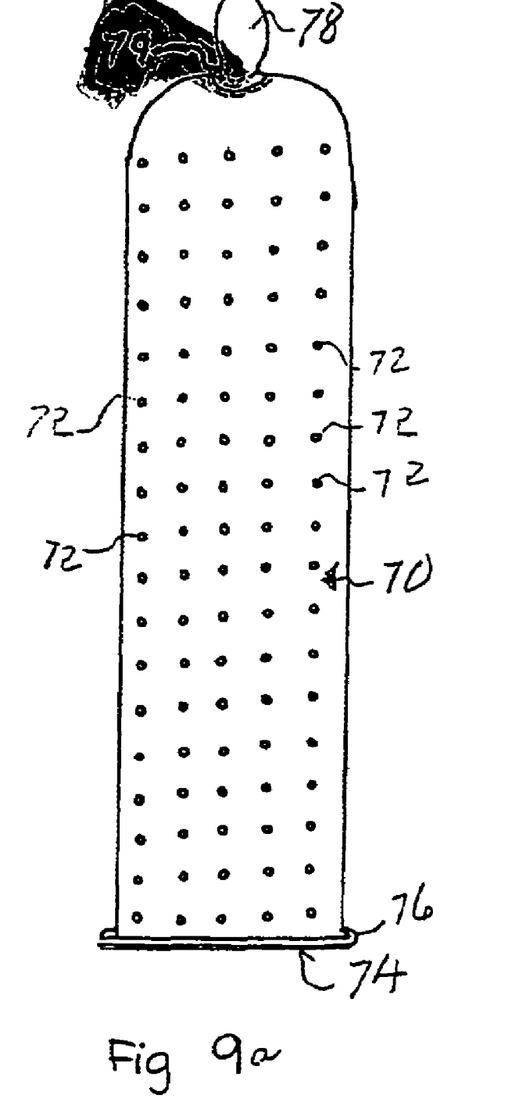
FIG. 9a is a side view of a condom used with the erectile aid of FIG. 1 showing a tip portion attached.
Figure 9B:
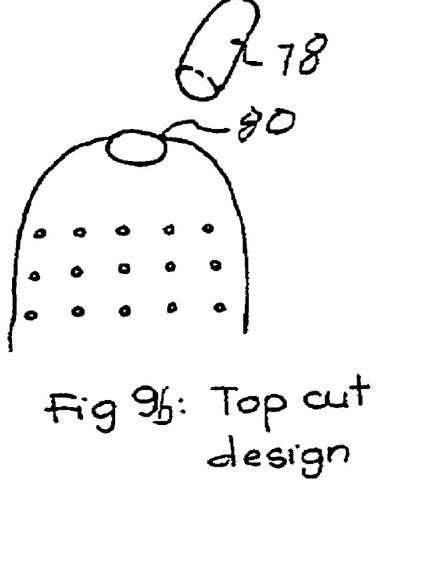
FIG. 9b is a side view of a portion of the condom in FIG. 9 showing a tip portion removed.

Referring now to FIGS. 9 and 9a, a condom 70 is shown which is used to protect the elastic bandage 10, 10' or 10" when the elastic bandage is wrapped around the penis 50. A preferable configuration, the condom 70 has an array of small air bubbles 52 arrayed on the surface thereof and has an open bottom end 74 with a thickened annular rim 76. The top end has a tip 78 to be torn or cut off for purposes to be explained hereinafter. The condom 70 is used to protect the elastic bandage 10, 10" or 10" from moisture and mechanical stress encountered during intercourse. In addition, the condom 70 can be used to prevent sexually transmitted diseases and pregnancy.

Figure 10A:
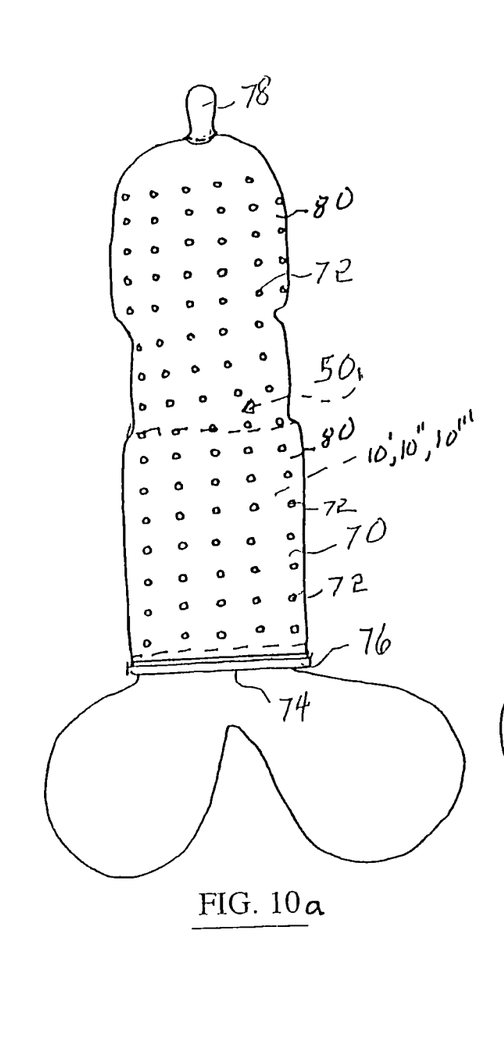
FIG. 10a is a bottom view showing a penis having a condom over both the penis and the erectal aid, the condom having its end portion intact.

Referring now to FIG. 10a, the condom 70 is shown rolled over the elastic bandage 10 to protect the bandage 10. In FIG. 10a the tip portion 78 is intact. The condom 70 may be used in this fashion to protect against sexually transmitted diseases and pregnancy.

Figure 10B:
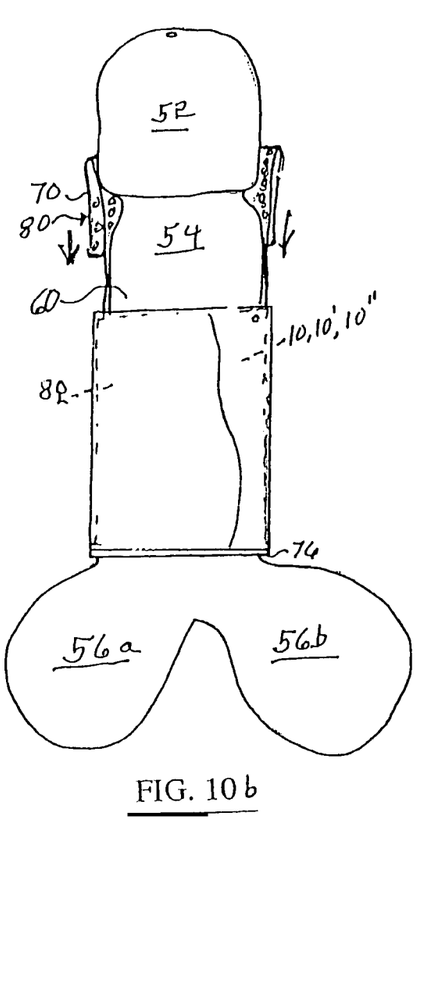
FIG. 10b is a bottom view showing a penis with a condom placed thereon first and the bandage coiled around the penis over the condom with the condom being thereafter rolled back over the bandage to expose the end of the penis.
Figure 10C:
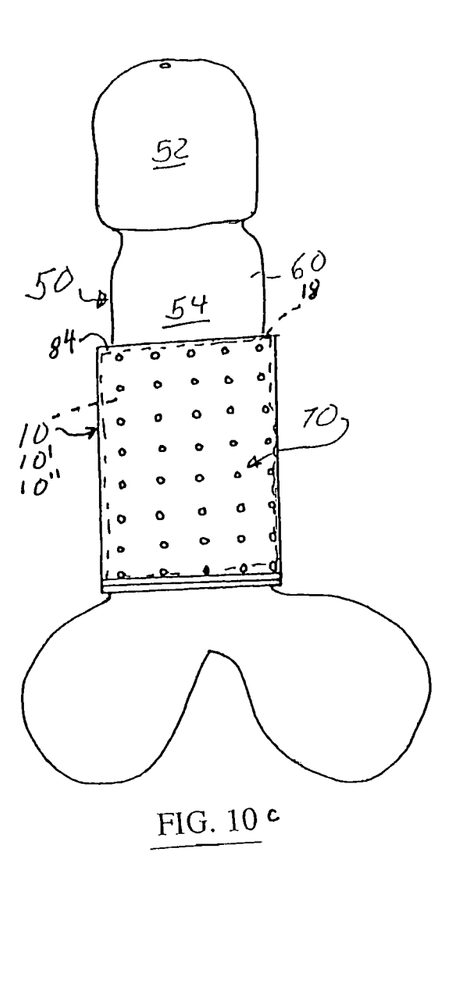
FIG. 10c is a bottom view of the penis of FIG. 10 showing the condom having the top portion removed and rolled back over the bandage, the bandage having been previously coiled around the condom.

FIGS. 10b and 10c show another embodiment of the invention wherein the condom 70 is applied first over the penis 50, and the bandage 10, 10' or 10" wrapped around the condom on the outside of the condom. To facilitate removal of the tip 78, there is a seam 90 which is opened by pulling a pull strip 91 that connects the tip to the condom 70. When the strip 91 is pulled the tip 78 separates along the seam 90 leaving the opening 80. The tip 78 of the condom 70 is removed as is shown in FIG. 9b and the condom is then rolled down over the glans 52 of the penis and the upper portion 60 of the shaft 54 by passing the glans of the penis through an opening 80 created by the removal of tip 78 by pulling a pull strip 79. Since the condom 70 is made of an elastic material, the opening 80 stretches to accommodate the glans 52 and shaft 54 of the penis 50. The upper portion 82 of the condom 70 is pulled down over the outside of the elastic bandage 10, 10' or 10" to cover the outside of the bandage and protect the bandage from moisture and mechanical stress during intercourse. In the arrangement of FIGS. 10b and 10c, the bandage 10, 10' or 10" is disposed between a lower half 82 and upper half 80 of the condom with the upper half of the condom 70 being turned inside out and fitting over the lower half, the outer edge 22 of the bandage being covered by a U-shaped bite 84 formed by the annular fold of the condom.

Utilization of the aforedescribed device addresses the problem of the valve in the base of the penis not keeping blood inside of the penis during and erection. When the valve is not functioning as designed, blood flows into the penis and out again and is not trapped by the valve use of products such as VIAGRA®, STAMINA® and others address this problem, but have side effects in some patients. The aforedescribed erectile aid and method compensate for valve leakage in order for an erection to be maintained.

The aforedescribed invention assists the valve and acts as a trap to keep the blood inside the penis 50 by allowing blood to flow, in but not, to flow out. The elastic bandages 10, 10' and 10" by being coiled urge the blood inside the penis toward the top of the penis (defined by the glans 52 and the outer part 60 of the shaft 54) so that the penis gets larger in diameter as well as longer. Moreover, by utilizing the arrangement in FIG. 10c, feeling of the experience is enhanced and patients find that their original and/or can return during the same coupling. Moreover, the erectile aid is simple, easy to put on or remove, inexpensive, has no side effects and has a natural appearance while working very well as an erectile aide.

From the foregoing description, one skilled in the art can easily ascertain the essential characteristics of this invention,

I claim:

1. An erection aid for maintaining stiffness in the penis comprising:
   an elastic bandage that has a selected length, width and thickness; the elastic bandage being self-adhering adapted to being coiled around the penis proximate the base of the penis in an overlapping relationship wherein the bandage adheres to itself; the elastic bandage having opposing first and second surfaces wherein the first surface of the bandage is folded upon itself along a length thereof and adhering thereto along a portion of the bandage to form a thickened portion of the bandage, which thickened portion applies localized pressure to the penis adjacent the base of the penis when the bandage is coiled around the penis and
   a condom having an open bottom and adapted to extend over the bandage when the bandage is coiled around the penis to provide a protective cover surrounding the elastic bandage.

2. The erection aid of claim 1 wherein the bandage has a width of about 2 inches and a length of about 8 to about 10 inches.

3. The erection aid of claim 1 wherein the bandage has a width of about 3 inches and a length of about 8 to 10 inches.

4. The erectile aid of claim 1 wherein the condom has an array of air bubbles thereon.

5. The erectile aid of claim 1 wherein the condom is adapted to be placed over the penis prior to wrapping the elastic, self-adhering bandage around the penis, and wherein the bandage is coiled over the condom after the condom is placed on the penis;
   the condom having a removable tip which is removed to provide an opening through which the penis passes as the condom is pulled down over the shaft of the penis and pulled over the wrapped bandage to cover the wrapped bandage while exposing an outer portion of the penis.

6. The erection aid of claim 5 wherein the bandage has a width of about 2 inches and a length of about 8 to about 10 inches.

7. The erection aid of claim 5 wherein the adhesive bandage has two side portions which are folded over a surface of the bandage to create a thickened area which functions as a pressure area when the bandage is copiled around the penis.

8. The erection aid of claim 7 wherein the bandage has a width of about 3 inches and a length of about 8 to 10 inches.

9. The erectile aid of claim 5 wherein the condom has an array of air bubbles thereon.

10. A method of maintaining an erect penis on a male wherein the erection is caused by blood flowing into the penis from the circulatory system of the male, comprising:
    stimulating the penis to achieve an erect penis;
    rolling a condom over the erect penis to cover the penis with the condom, the condom having an inside surface engaging the penis and an outside surface exposed;
    wrapping a self-adhering elastic bandage having a longitudinal extent around the outside surface of the condom to prevent blood from returning from the penis to the circulatory system, the self-adhering elastic bandage having a thickened portion extending longitudinally with respect thereto, the thickened portion pressing against the penis at a pressure location near the base of the penis
    pulling the condom inside out back over the penis by passing the glans and shaft of the penis through an opening in the end of the condom, and
    overlapping the self-adhering elastic bandage with the outside surface of the condom to dispose the elastic bandage between the outside and inside surfaces of the condom while uncovering at least the glans.

11. The method of claim 10 wherein the self-adhering elastic bandage is spaced from the glans to uncover a portion of the shaft as well when the condom is pulled back over the self-adhering bandage.

12. The method of claim 11 comprising increasing the length and diameter of the penis out board of the pressure location by holding the thickened portion pressed against the pressure location by adhering the self-adhering bandage to itself.

13. The method of claim 12 wherein the thickened portion is created by folding the side portion of the bandage back over a surface of the bandage.

14. A method of sustaining an erect penis in a male comprising wrapping an erect penis with a self-adhering elastic bandage having opposing first and second surfaces, covering the self-adhering elastic bandage with a condom and applying more pressure at a location adjacent to the base of the penis then elsewhere with the self-adhering elastic bandage to cause the penis to increase in diameter and length outboard of the bandage by folding the first surface of the bandage upon itself along a length thereof and adhering thereto along a portion of the bandage.

* * * * *